US00PP14338P29

(12) United States Plant Patent
Post

(10) Patent No.: US PP14,338 P2
(45) Date of Patent: Dec. 2, 2003

(54) CHRYSANTHEMUM PLANT NAMED 'ORINOCO'

(50) Latin Name: *Chrysanthemum X morifolium*
Varietal Denomination: Orinco

(75) Inventor: Arie Gerard Post, 's-Gravenzande (NL)

(73) Assignee: Deliflor Royalties, B.V., Maasdijk (NL)

( * ) Notice: Subject to any disclaimer, the term of this patent is extended or adjusted under 35 U.S.C. 154(b) by 0 days.

(21) Appl. No.: 10/232,886

(22) Filed: Aug. 31, 2002

(51) Int. Cl.[7] ..... A01H 5/00
(52) U.S. Cl. ..... Plt./286
(58) Field of Search ..... Plt./286

*Primary Examiner*—Bruce R. Campell
*Assistant Examiner*—Annette Para
(74) *Attorney, Agent, or Firm*—C. A. Whealy

(57) ABSTRACT

A new and distinct cultivar of Chrysanthemum plant named 'Orinoco', characterized by its upright and strong flower stems; uniform and freely flowering habit; daisy-type inflorescences; red purple and white bi-colored ray florets; yellow green-colored disc florets; natural season flowering in November in the Northern Hemisphere; and good postproduction longevity.

2 Drawing Sheets

Botanical classification/cultivar designation: *Chrysanthemum×morifolium* cultivar Orinoco.

BACKGROUND OF THE INVENTION

The present invention relates to a new and distinct cultivar of Chrysanthemum plant, botanically known as *Chrysanthemum×morifolium*, commercially grown as a cut flower Chrysanthemum and hereinafter referred to by the name 'Orinoco'.

The new cultivar is a product of a planned breeding program conducted by the Inventor in 's-Gravenzande, The Netherlands. The objective of the breeding program is to create new cut flower Chrysanthemum cultivars having inflorescences with desirable inflorescence forms, attractive floret colors and good postproduction longevity.

The new Chrysanthemum originated from a cross-pollination made in 's-Gravenzande, The Netherlands, of a proprietary selection of Chrysanthemum identified as code number DB 8882, not patented, as the female, or seed, parent with the Chrysanthemum cultivar Bennie Jolink, not patented, as the male, or pollen, parent. The new Chrysanthemum was discovered and selected by the Inventor as a single flowering plant within the progeny of the stated cross-pollination grown in a controlled environment in 's-Gravenzande, The Netherlands in November, 1999.

Asexual reproduction of the new cultivar by terminal cuttings taken in a controlled environment in 's-Gravenzande, The Netherlands since November, 1999, has shown that the unique features of this new Chrysanthemum are stable and reproduced true to type in successive generations.

SUMMARY OF THE INVENTION

The cultivar Orinoco has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Orinoco'.

These characteristics in combination distinguish 'Orinoco' as a new and distinct cultivar:

1. Upright and strong flowering stems.
2. Uniform and freely flowering habit.
3. Daisy-type inflorescences.
4. Red purple and white bi-colored ray florets and yellow green-colored disc florets.
5. Natural season flowering in November in the Northern Hemisphere.
6. Good postproduction longevity.

Plants of the new Chrysanthemum can be compared to plants of the female parent, the selection DB 8882. In side-by-side comparisons conducted in 's-Gravenzande, The Netherlands, plants of the new Chrysanthemum differed from plants of the selection DB 8882 in the following characteristics:

1. Plants of the new Chrysanthemum were more vigorous than plants of the selection DB 8882.
2. Plants of the new Chrysanthemum had larger inflorescences than plants of the selection DB 8882.
3. Plants of the new Chrysanthemum had red purple and white bi-colored ray florets whereas plants of the selection DB 8882 had solid red-colored ray florets.
4. Plants of the new Chrysanthemum had longer peduncles than plants of the selection DB 8882.

Plants of the new Chrysanthemum can be compared to plants of the male parent, the cultivar Bennie Jolink. In side-by-side comparisons conducted in 's-Gravenzande, The Netherlands, plants of the new Chrysanthemum differed from plants of the cultivar Bennie Jolink in the following characteristics:

1. Plants of the new Chrysanthemum were more vigorous and more uniform than plants of the cultivar Bennie Jolink.
2. Plants of the new Chrysanthemum flowered about two days earlier than plants of the cultivar Bennie Jolink.
3. Ray florets of plants of the new Chrysanthemum were more narrow than ray florets of plants of the cultivar Bennie Jolink.

4. Ray florets of plants of the new Chrysanthemum were darker red purple in color than ray florets of plants of the cultivar Bennie Jolink.

Plants of the new Chrysanthemum can be compared to plants of the cultivar Harlekijn, disclosed in U.S. Plant Pat. No. 6,291. In side-by-side comparisons conducted in 's-Gravenzande, The Netherlands, plants of the new Chrysanthemum differed from plants of the cultivar Harlekijn in the following characteristics:

1. Plants of the new Chrysanthemum flowered about two days earlier than plants of the cultivar Harlekijn.
2. Ray floret color of plants of the new Chrysanthemum was more vibrant and darker red purple than ray floret color of plants of the cultivar Harlekijn.
3. Disc florets of plants of the new Chrysanthemum developed slower than disc florets of plants of the cultivar Harlekijn.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Orinoco'.

The photograph at the top of the second sheet is a close-up view of a typical flowering stem of the cultivar 'Orinoco'.

The photograph at the bottom of the second sheet is a close-up view of the lower and upper surfaces of typical leaves of 'Orinoco'.

DETAILED BOTANICAL DESCRIPTION

The aforementioned photographs and following observations and measurements describe non-pinched plants grown in a glass-covered greenhouse in 's-Gravenzande, The Netherlands under photoinductive short day/long night conditions and cultural practices which approximate those generally used in commercial cut flower Chrysanthemum production. Plants were about 11 weeks old when the photographs, observations and measurements were taken. During the production of the plants, day temperatures averaged about 18° C. and night temperatures averaged about 19° C. Measurements and numerical values represent averages for typical flowering plants. In the following description, color references are made to The Royal Horticultural Society Colour Chart, 1995 Edition, except where general terms of ordinary dictionary significance are used.

Botanical classification: *Chrysanthemum×morifolium* cultivar Orinoco.

Parentage:

*Female, or seed, parent.*—Proprietary selection of *Chrysanthemum×morifolium* identified as code number DB 8882, not patented.

*Male, or pollen, parent.*—*Chrysanthemum×morifolium* cultivar Bennie Jolink, not patented.

Propagation:

*Type.*—Terminal tip cuttings.

*Time to initiate roots.*—Summer: About 5 days at 20° C. Winter: About 6 days at 20° C.

*Root description.*—White, thick and fibrous.

*Rooting habit.*—Freely branching.

Plant description:

*Appearance.*—Cut flower Chrysanthemum with upright and strong flowering stems. Moderately vigorous.

*Plant height.*—About 80 cm.

*Stem texture.*—Pubescent.

*Stem color.*—144A.

*Foliage descrption.*—Leaf arrangement: Alternate; single. Length: About 13.5 to 14.5 cm. Width: About 10 cm. Apex: Mucronate. Base: Rounded. Margin: Palmately lobed, sinuate. Texture, upper and lower surfaces: Leathery; slightly pubescent. Venation pattern: Pinnate. Color: Young foliage, upper surface: 139A. Young foliage, lower surface: 137B. Fully expanded foliage, upper surface: 137A. Fully expanded foliage, lower surface: 147B. Venation, upper and lower surfaces: 146C. Petiole length: About 2.5 to 3 cm. Petiole diameter: About 2 mm. Petiole color, upper and lower surfaces: 146C.

Inflorescence description:

*Appearance.*—Daisy-type inflorescence form with elongated oblong ray florets. Inflorescences borne on terminals above foliage, arising from leaf axils. Disk and ray florets develop acropetally on a capitulum. About 17 inflorescences per flowering stem. Inflorescences persistent. Inflorescences not fragrant.

*Flowering response.*—Under natural season conditions, plants flower in November in the Northern Hemisphere. Plants flower about 48 to 49 days under photoinductive short day/long night conditions.

*Postproduction longevity.*—Inflorescences maintain good substance for about 5 weeks on the plant and for about 3.5 weeks as a cut flower.

*Inflorescence bud* (*stage of showing color*).—Height: About 6 mm. Diameter: About 8 mm. Shape: Oblate. Phyllary color: 137C.

*Inflorescence size.*—Diameter: About 7.5 cm. Depth (height): About 2 cm. Disc diameter: About 1.5 cm.

*Ray florets.*—Shape: Elongated oblong. Length: About 3.4 cm. Width: About 1.3 cm. Apex: Rounded. Base: Obtuse. Margin: Entire. Texture, upper and lower surfaces: Smooth, glabrous, satiny. Number of ray florets per inflorescence: About 27 to 40. Color: When opening, upper and lower surfaces: 59A; apical margins, 158D. Opened inflorescence, upper and lower surfaces: 61A; apical margins, 158D.

*Disc florets.*—Shape: Tubular, apex dentate. Length: About 5 mm. Width: About 1 mm. Quantity per inflorescence: About 159 to 169. Color: Immature: 145C. Mature: 145D.

*Lateral peduncles.*—Length: First peduncle: About 6 cm. Fourth peduncle: About 8 cm. Diameter: About 2 mm. Texture: Pubescent. Strength: Strong. Color: 148A.

*Reproductive organs.*—Androecium: Present on disc florets only. Anther color: 14A. Pollen amount: Moderate. Pollen color: 14A. Gynoecium: Present on both ray and disc florets.

*Seed/fruit.*—Seed nor fruit production has not been observed.

Disease/pest resistance: Plants of the new Chrysanthemum have not been shown to be resistant to pathogens and pests common to Chrysanthemums.

It is claimed:

1. A new and distinct cultivar of Chrysanthemum plant named 'Orinoco', as illustrated and described.

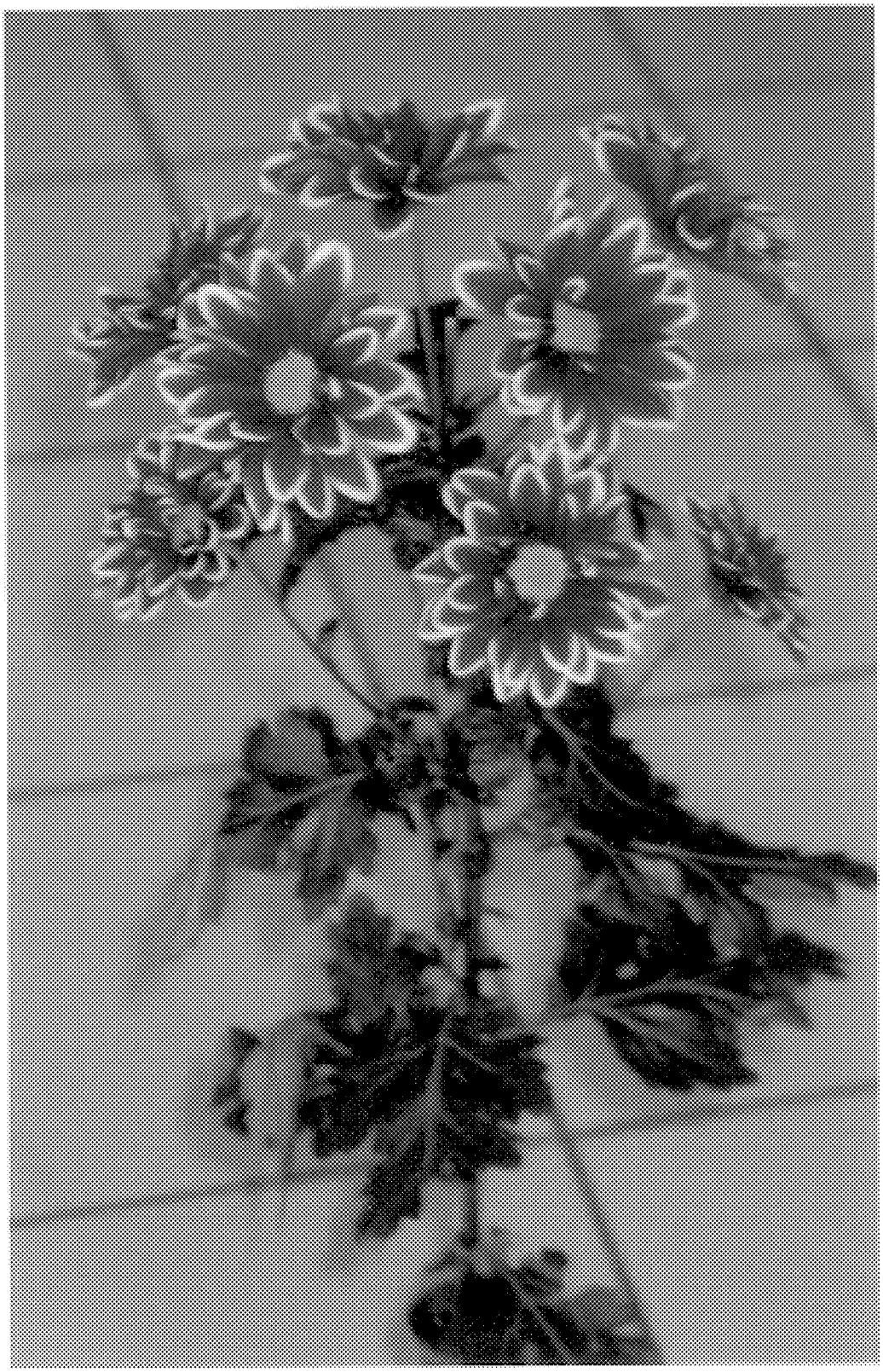

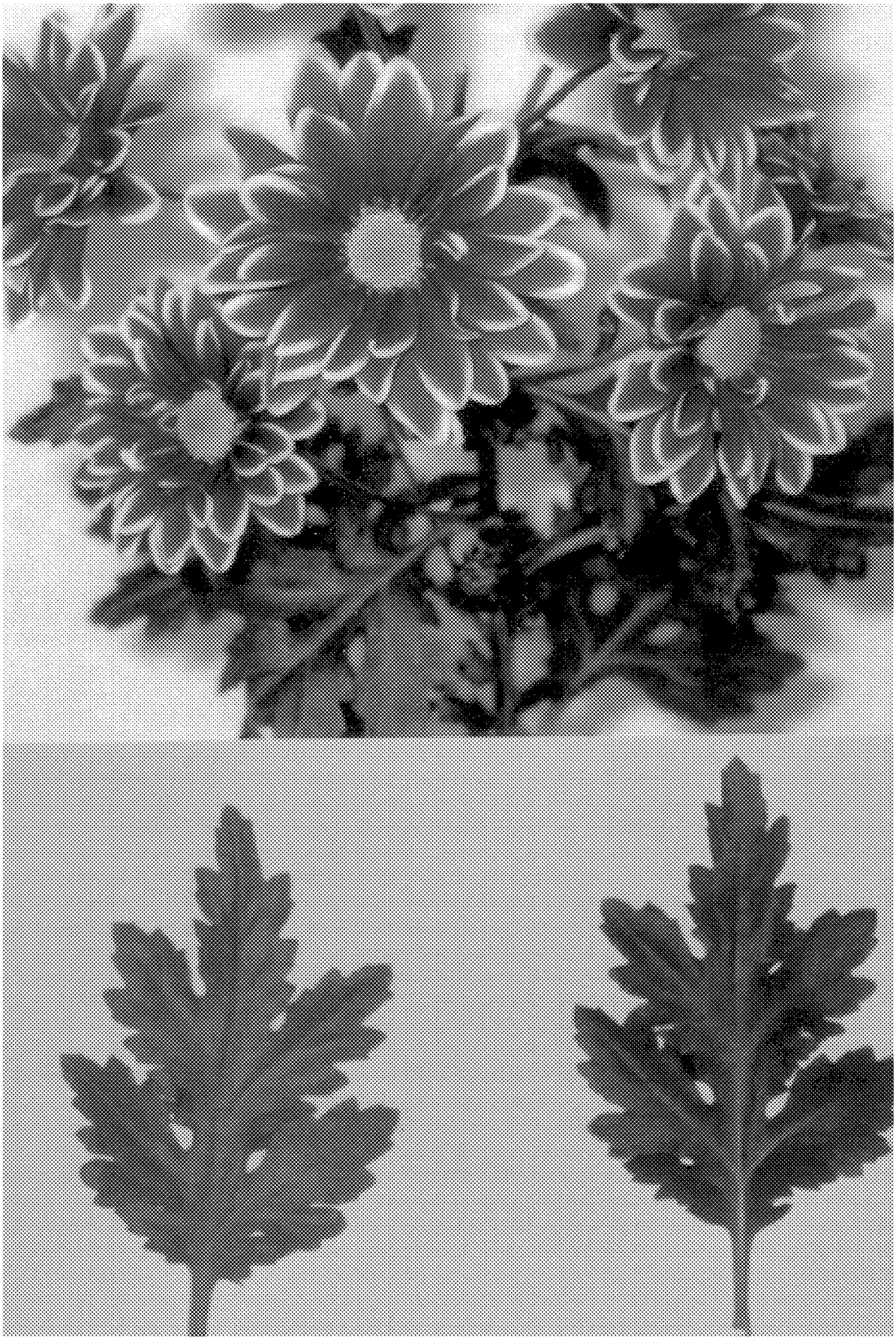

* * * * *